United States Patent
Uchihori et al.

[11] Patent Number: 5,206,172
[45] Date of Patent: Apr. 27, 1993

[54] COUNTERFLOW PREVENTION SYSTEM FOR A FERMENTATION TANK

[75] Inventors: Yuji Uchihori, Hikari; Goichi Aimoto, Kudamatsu; Toshihiko Nakayama, Tokuyama, all of Japan

[73] Assignee: Takeda Chemical Industries, Ltd., Osaka, Japan

[21] Appl. No.: 714,935

[22] Filed: Jun. 13, 1991

[30] Foreign Application Priority Data

Jun. 13, 1990 [JP] Japan .................................. 2-156519

[51] Int. Cl.[5] .............................................. C12M 1/12
[52] U.S. Cl. ...................................... 435/311; 435/313; 435/800; 422/113
[58] Field of Search ................ 435/207, 302, 311, 800, 435/289, 313, 314, 315, 316, 812; 422/38, 39, 26, 112, 113; 137/216; 261/26, 121.17, 121.2, 122.1

[56] References Cited

U.S. PATENT DOCUMENTS

| | | | |
|---|---|---|---|
| 2,338,227 | 1/1944 | Boeckelev et al. | 422/26 |
| 3,445,341 | 5/1969 | Freedman et al. | 435/311 |
| 3,901,265 | 8/1975 | Groombridge | 137/218 |
| 4,324,762 | 4/1982 | Redikultsev et al. | 435/311 |
| 4,868,124 | 9/1989 | Rietschel et al. | 435/311 |
| 4,915,606 | 4/1990 | Shimokawa | 422/26 |

Primary Examiner—Michael G. Wityshyn
Assistant Examiner—Wiliam H. Beisner
Attorney, Agent, or Firm—Koda and Androlia

[57] ABSTRACT

A possible counterflow of a fermenting solution (8) from a fermentation tank (1) into a heating medium supply pipe (2), which counterflow may be caused by a pressure difference arising between the inner space (7) of the tank (1) and the pipe (2) after the supply of a heating medium is finished, is prevented by making the pressure difference disappear with a check valve (6) connected to the pipe (2) in the direction from the inner space (7) of the tank (1) to the pipe (2).

2 Claims, 2 Drawing Sheets

COUNTERFLOW PREVENTION SYSTEM FOR A FERMENTATION TANK

BACKGROUND OF THE INVENTION

The present invention relates to a counterflow prevention system to be provided in a fermentation tank, more particularly to a system for preventing a fermentation medium contained in a fermentation tank from being pressed back therefrom owing to a possible pressure increase in the fermentation tank.

It is essentially important, in fermentation industry, that the fermentation tanks in use have their inside, including the fermentation medium or solution contained therein, kept completely free from any kind of sundry microorganism. The work of fermentation may therefore be said to begin substantially with sterilization of the fermentation medium. The sterilization is carried out in general by heating the fermentation medium with a heating medium such as hot water or steam introduced through a sparger installed at the bottom portion of each fermentation tank so as to be immersed in the fermentation medium. The thus sterilized fermentation medium, after being cooled down to an appropriate temperature, is inoculated with purposeful seed microorganisms, and then put into a process of fermentation. Further, in the case of the microorganisms being aerobic, the fermentation medium is aerated with clean air (made free from sundry microorganisms introduced through the above sparger, which has a selective connection with a source of the heating medium and with an air source through piping. Therefore, the fermentation tank has its inner temperature and pressure varied, as is easily supposed, during the above brief sterilization and aeration work, causing a possible pressure increase in the tank to show a tendency of pressing the fermentation medium back into the piping connecting the sparger to the above sources of heating medium and air. The fermentation medium, if it counterflows into the piping, contaminates elements such as operation valves and air filters positioned midway in the piping, and deteriorates the performance of the elements, causing sundry microorganisms to be recurrently grown there.

A conventional method of eliminating such contamination is to provide various instruments for precisely controlling the pressure manually or automatically in the fermentation tank and the piping. According to this method, however, the entire fermentation system is made not only expensive but also complex.

Another conventional method commonly used is to insert a conventional check valve assembly to the piping in series. This method is described in the following with reference to FIGS. 3, 4 and 5.

FIG. 3 shows a conceptual view illustrating the state that a heating medium is supplied to a tank A from a heating medium source (not shown) through a pipe C, a check valve assembly D and a pipe B. The check valve assembly D consists of a first check valve E, an exhaust valve G and a second check valve F, all connected in series with the exhaust valve G positioned between the first and the second check valves E and F. These two check valves E and F are, of course, directed so that the heating medium may flow only in the direction from the heating medium source (not shown) to the tank A. Next, the structure and function of the check valve assembly D are described in detail with reference to FIGS. 4 and 5, which show the states of the assembly allowing the heating medium to flow and of checking the flow of the medium, respectively. According to FIGS. 4 and 5, the check valve assembly D consists essentially of two valve cases 10 and 20 connected to each other at a right angle through a connecting hole 14, two valve plates 11 and 12 vertically movable in the valve case 10, and a valve plate 21 horizontally movable in the valve case 20. The valve plates 11, 12 and 21 are constructed and arranged, by means of their respective springs 11$a$, 12$a$ and 21$a$, so as to be forced toward valve sheets 11$b$, 12$b$ and 12$b$ formed within the valve cases 11 and 20 in correspondence respectively with the valve plates 11, 12 and 21. Further, the valve case 10 is provided both with an opening to which is connected an inlet pipe C (which corresponds to the pipe C in FIG. 3) so as to face the valve plate 11 and with an exhaust opening 13 so as to face the valve plate 12, while the valve case 20 is provided on its side wall with an outlet pipe B (which corresponds to the pipe B in FIG. 3). In such a structure of the check valve assembly, the valve plate 11 and valve seat form the first check valve E (FIG. 3); the valve plate 12 and valve seat 12$b$ form the exhaust valve G (FIG. 3); and the valve plate 21 and valve seat 21$b$ form the second check valve F (FIG. 3).

With the heating medium supplied through the inlet pipe C, the valve plates 11 and 21 are pressed respectively downward and leftward under the pressure of the medium, and consequentially there is formed in the assembly, as is illustrated in FIG. 5, a passage for the medium, with the exhaust opening 13 being closed which results from the downward displacement of the valve plate 12 having a connection with the valve plate 11. When the supply of the heating medium is stopped, the passage is closed, as is illustrated in FIG. 4, by both the valve plates 11 and 21, with the exhaust opening 13 being open.

According to this check valve assembly, even if the pressure on the outlet pipe side is increased so that the valve plate 21 malfunctions, a possible counterflow from the tank is not only stopped by the valve plate 11 but also exhausted into the atmosphere through the connecting opening 14 and the exhaust opening 13. Further, even when the inlet pipe C has its inner pressure made negative for any reason so that the valve plate 11 also malfunctions, the counterflow from the tank does not flow into the inlet pipe side, though the atmospheric air may be inhaled.

However, also according to a check valve assembly of this type, the assembly can not be prevented from being contaminated by the liquid pressed back from the tank because the liquid comes into contact with the inside walls and members of the assembly.

OBJECTS AND SUMMARY OF THE INVENTION

The present invention aims at solving the disadvantages accompanying the above described conventional counterflow prevention system provided in a fermentation tank, and makes it an object to provide an improved system for preventing a counterflow of the fermentation medium into the piping even if a pressure difference develops between the tank and the piping.

Another object of the present invention is to make up such an improved counterflow prevention system in a simple construction by using a commercially available known check valve.

To achieve the above objects, the counterflow prevention system according to the present invention comprises a check valve branching out from a heating medium supply pipe introduced into a fermentation tank from an external heating medium source. The heating medium supply pipe is connected to a ring sparger provided in the fermentation tank so as to be immersed in a fermentation medium contained in the tank, while the above check valve is located above the surface of the fermentation medium, with the allowable flow direction directed from the space in the tank to the heating medium supply pipe.

Accordingly, if the inner pressure of the fermentation tank becomes higher than that of the heating medium supply pipe after the supply of a heating medium has been stopped, the check valve opens to equalize the inner pressure of the tank with that of the pipe, preventing the fermentation medium from being pressed into the heating medium supply pipe.

BRIEF DESCRIPTION OF THE DRAWINGS

The present invention is described in further detail in the following with reference to some of the accompanying drawings, in which.

DETAILED DESCRIPTION OF THE INVENTION

Figure 1:
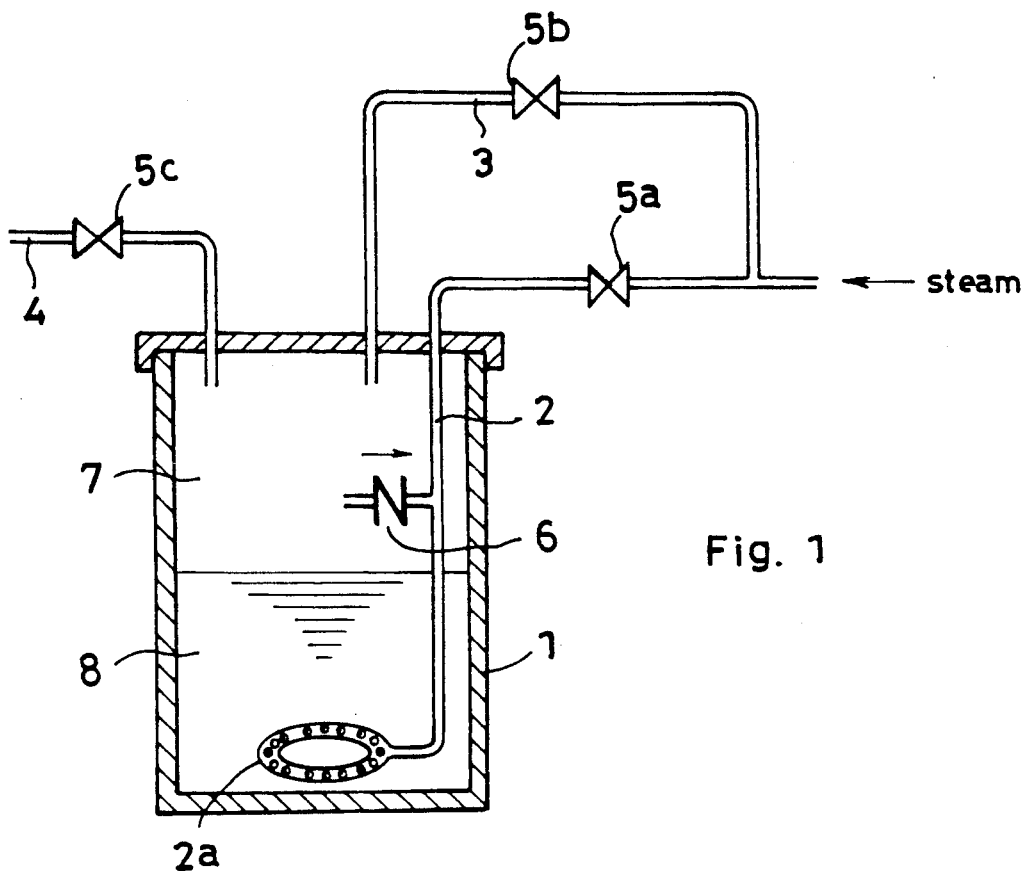
FIG. 1 schematically shows the state that the counterflow prevention system according to the present invention is applied to a fermentation tank.

Referring to FIG. 1, in which is shown as an embodiment of the present invention, an invented counterflow prevention system has its essential part constructed with a check valve 6 and a heating medium supply pipe 2, which is introduced from a not shown hot steam source or air source into a fermentation tank 1 with the lower end connected to a ring sparger 2a located so as to be immersed in a fermentation medium 8 contained in the tank 1. The check valve 6 is provided so as to branch out from the heating medium supply pipe 2 at an appropriate level above the surface of the fermentation medium 8. The check valve 6 has its flow direction directed to the pipe 2 from a space 7 formed on the surface of the solution 8 in the tank 1. In addition to the above, a pressure keeping pipe 3 is introduced into the space 7 in the tank 1, branching out from the heating medium supply pipe 2, while an exhaust pipe 4 is let out from the space 7. Further, the pipes 2, 3 and 4 are provided midway with control valves 5a, 5b and 5c, respectively.

Next, the operation of the present embodiment is described in conjunction with the process of sterilizing the fermentation medium 8 put in the fermentation tank 1. In the first plate, a stream of hot steam as a heating medium is introduced into the medium 8 through the pipe 2 and the ring sparger 2a, with the valve 5a fully opened, the valve 5b slightly opened and the valve 5c kept slightly opened after being fully opened. After the solution 8 is thus heated up to a sterilizing temperature (higher than 100° C.), the valve 5a is closed to stop the supply of the hot steam, and the medium 8 is left as it is for a while with the valve 5b opened and the valve 5c closed. After the sterilization of the solution 8 is completed, the hot fermentation medium 8 is cooled down by a cooler (not shown) to an appropriate fermentation temperature. During this process of cooling down the medium 8 to an appropriate fermentation temperature, the steam remaining in the pipe 2 is also cooled and condensed. Accordingly, the inner pressure of the pipe 2 is decreased to a value lower than the pressure of the space 7 in the tank 1, and then the check valve is opened causing a pressure difference between the pipe 2 and the space 7 to disappear. In this manner a counterflow of the medium 8 into the pipe 2 through the ring sparger 2a is prevented.

Figure 2:
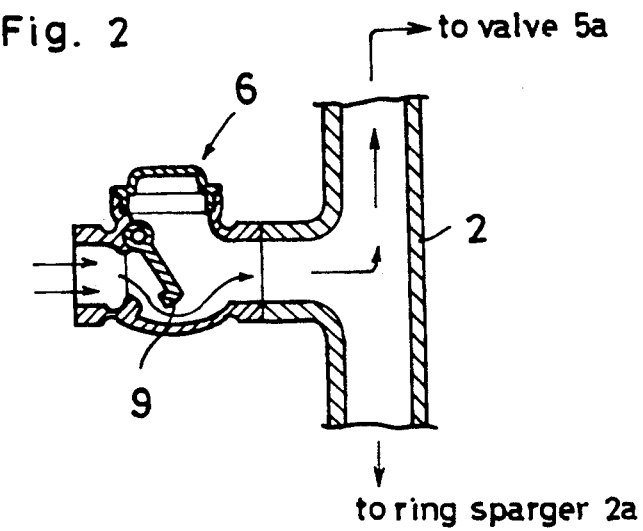
FIG. 2 shows a detailed cross-sectional view of a swing type check valve usable in the present invention.
Figure 3:
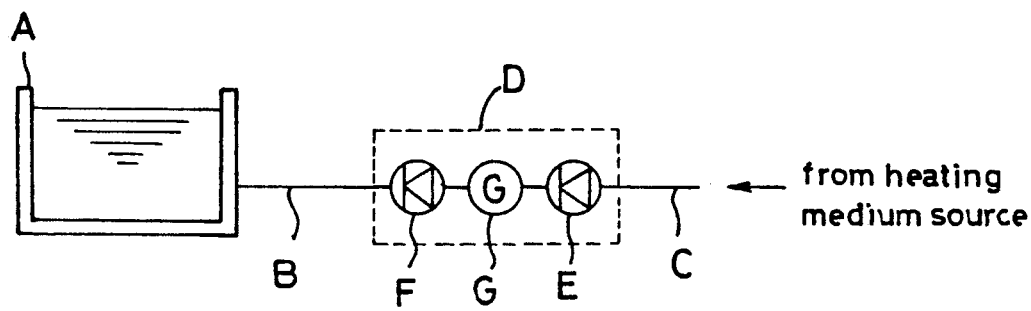
FIG. 3 shows a conceptual structure of a conventional counterflow prevention system applied to a fermentation tank.
Figures 4, 5:
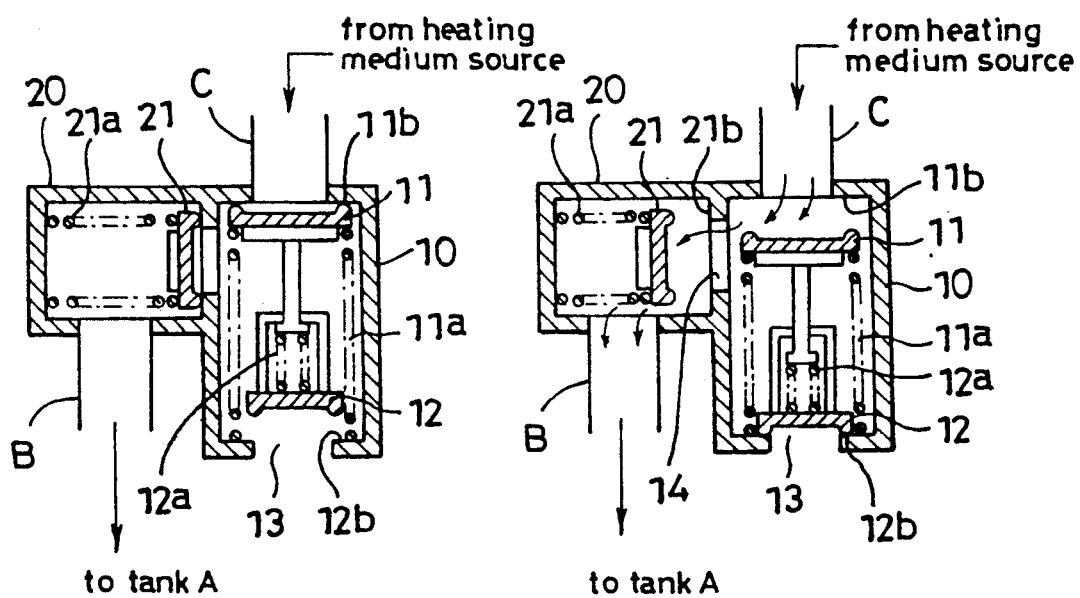
FIGS. 4 and 5 shows cross-sectional views of a check valve assembly used in the system shown in FIG. 3.

In the embodiment described above, any type of check valve can be used as the check valve 6, including a swing type check valve as shown in FIG. 2. In the case of a swing type check valve, however, the valve body is necessarily kept horizontal so that the valve plate 9 functions properly (FIG. 2).

Needless to say, the present invention can be further applied to any pressure vessel to which is connected a pipe for blowing a gas into the vessel.

We claim:

1. A system for preventing back flow of a fermentation medium contained in a fermentation tank comprising:
   a fermentation tank containing a fermentation medium;
   a sparger submerged in said fermentation medium;
   a heating medium introduction pipe connected to said sparger for introducing a heating medium into said fermentation medium through said sparger;
   a branch pipe branching out from said heating medium introduction pipe so as to provide flow communication between an interior of the tank at a level above the liquid surface of said fermentation medium and said heating medium introduction pipe; and
   a check valve connected to said branch pipe so as to make gas or vapor flow only in the direction from said interior of the tank toward said heating medium introduction pipe.

2. A system as defined in claim 1, wherein said check valve is of a swing type.

* * * * *